United States Patent [19]

Moreau et al.

[11] Patent Number: 5,462,927
[45] Date of Patent: Oct. 31, 1995

[54] PEPTIDES AIDING NERVE REGENERATION

[75] Inventors: Jacques-Pierre Moreau, Upton, Mass.; David H. Coy, New Orleans, La.

[73] Assignee: The Administrators of the Tulane Educational Fund, New Orleans, La.

[21] Appl. No.: 990,555

[22] Filed: Dec. 14, 1992

Related U.S. Application Data

[63] Continuation-in-part of Ser. No. 431,339, Nov. 3, 1989, abandoned, which is a continuation-in-part of Ser. No. 728,847, Apr. 30, 1985, abandoned.

[51] Int. Cl.$^6$ .................. A61K 38/00; C07K 7/00; C07K 7/06; C07K 14/68
[52] U.S. Cl. .................. 514/17; 530/326; 530/329; 514/16
[58] Field of Search .................. 530/326, 329; 514/17

[56] References Cited

U.S. PATENT DOCUMENTS

| | | | |
|---|---|---|---|
| 3,479,333 | 11/1969 | Greven | 433/219 |
| 3,842,064 | 10/1974 | Greven | 530/329 |
| 3,853,836 | 12/1974 | Greven | 530/330 |
| 3,856,770 | 12/1974 | Greven | 530/329 |
| 4,110,320 | 8/1978 | Greven | 530/326 |

FOREIGN PATENT DOCUMENTS 90319169  6/1991  European Pat. Off.

OTHER PUBLICATIONS

Sawyer, et al, J. Med. Chem. 25 (1982) 1022–1027.
Saint–Come, et al, Chem Abstr. vol. 103 11663q (1985).
Bijlsma et al, Eur. J. Pharm. 76 (1981) 73–79.
Bijlsma et al, Eur. J. Pharm. 92 (1983) 231–236.
Sawyer et al. J. Med. Chem. 25 (1982) 1022–1027.
Geissler et al, *New England Journal of Medicine*, vol. 324, p. 1991.
Stein et al, Act H(4–10) Analog Potentiates Cognitive and Morphological Recovery After Frontal Cortex Lesions in Adults Rats, 1991, pp. 193–207.
Knittel et al., J. Med. Chem. 26 (1983) 125–129.
Wilkes et al., Int. J. Peptide Protein Res. 22 (1983) 313–324.
Cody et al., J. Med. Chem. 27 (1984) 1186–1190.
Saint–Come et al., Chem. Abstr., vol. 104:123443v (1986).
Saint–Come et al., Chem. Abstract, vol. 103:116639q (1985).
Engel et al., Chem. Abstracts, vol. 101, 1984, pp. 287–288 Abst. No. 3306u & Pept. Struct. Funct., Proc. Am. Pept. Symp., 8th (1983) 723–6.
Hruby et al., Chem. Abst. vol. 103, 1985 p. 68, Abst. No. 98844w, Columbus, Ohio & Pept., Proc. Eur. Pept. Symp., 18th 1984, 505–8.
Staples et al., Chem. Abst. vol. 105, 1986, p. 97, Abt. No. 18672s, Columbus, Ohio, U.S. & Pept. Struct. Funct., Proc. Am. Pept. Symp. 9th, 1985, 691–4.
Stewart et al., Chemical Abst. vol. 94, 1981, p. 94, Abst. 25415t, Columbus, Ohio, U.S. & LRH and ACTH & Pept. Struct. Biol. Funct., Proc. Am. Pept. Symp. 6th 1979, 761–4.

*Primary Examiner*—Jill Warden
*Assistant Examiner*—S. G. Marshall
*Attorney, Agent, or Firm*—Fish & Richardson

[57] ABSTRACT

Biologically active peptides are disclosed of the formula: $A^1-A^2-A^3-A^4-Phe-Arg-TrP-A^5$, or a pharmaceutically acceptable salt thereof; $A^1$ is H or acetyl; $A^2$ is Ala, or D—Ala; $A^3$ is Glu or Gln; and $A^4$ is His or Tyr; $A^5$ is $NH_2$, Gly—$NH_2$, or D—Ala—$NH_2$. Pharmaceutical compositions containing these peptides are capable of promoting nerve regeneration and increasing muscle mass or preventing muscle atrophy following an injury.

12 Claims, 4 Drawing Sheets

| NERVE LESION | FOOT LENGTH | ANKLE DORSILFLEXION | TOE SPREAD | GAIT ABNORMALITY |
|---|---|---|---|---|
| NORMAL |  |  |  | NONE |
| POSTERIOR TIBIAL |  |  |  | FOOT LENGTH TOE SPREAD ANKLE DORSILFLEXION |
| PERONEAL | 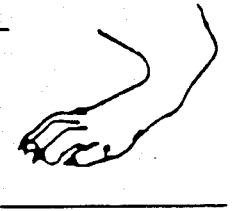 |  |  | FOOT LENGTH TOE SPREAD ANKLE DORSILFLEXION |
| SCIATIC |  |  |  | FOOT LENGTH TOE SPREAD ANKLE DORSILFLEXION |
FIG. 1

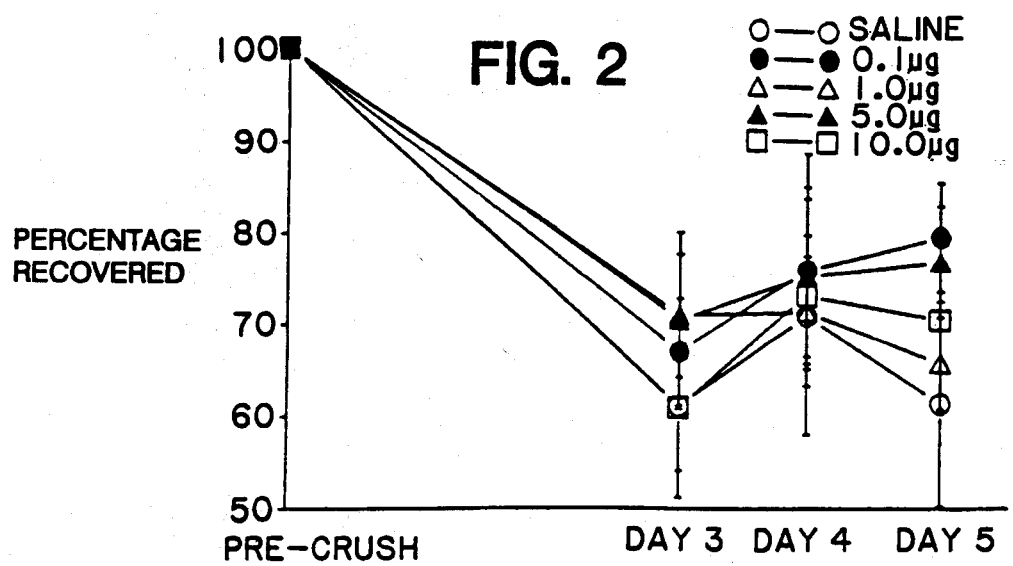
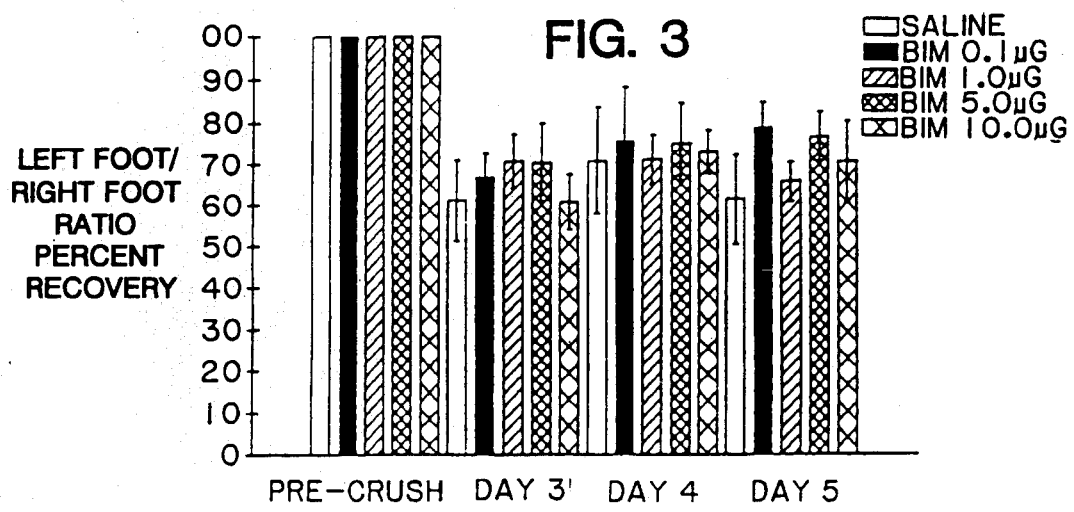

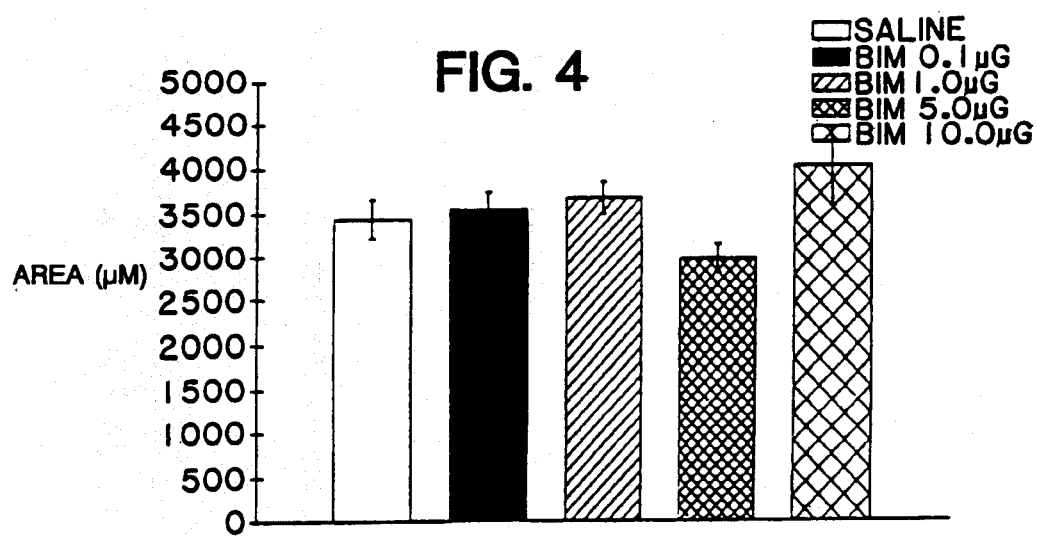
FIG. 4
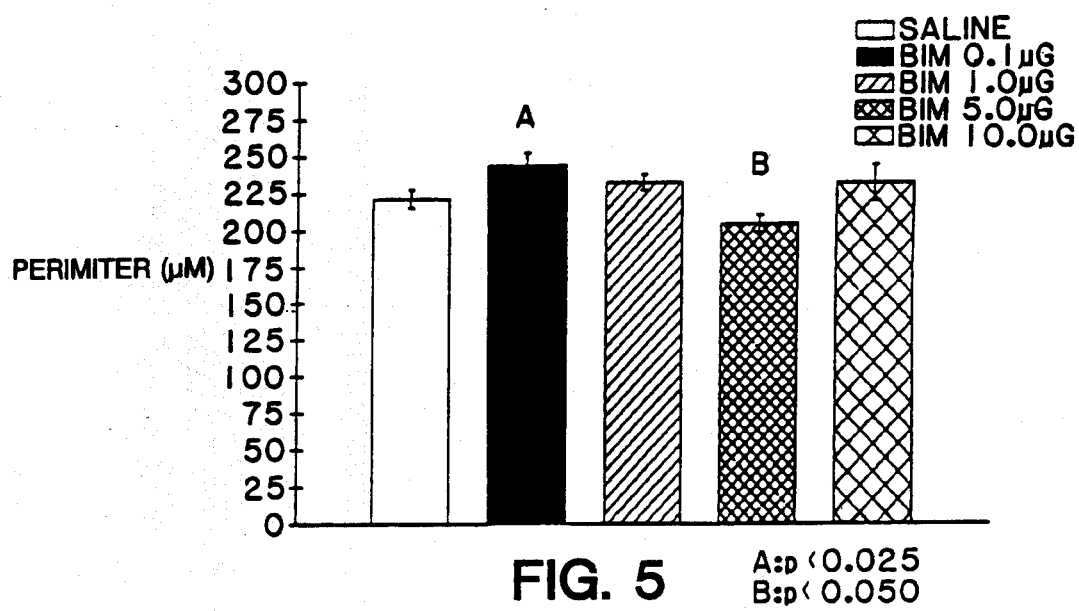
FIG. 5   A: p < 0.025
B: p < 0.050

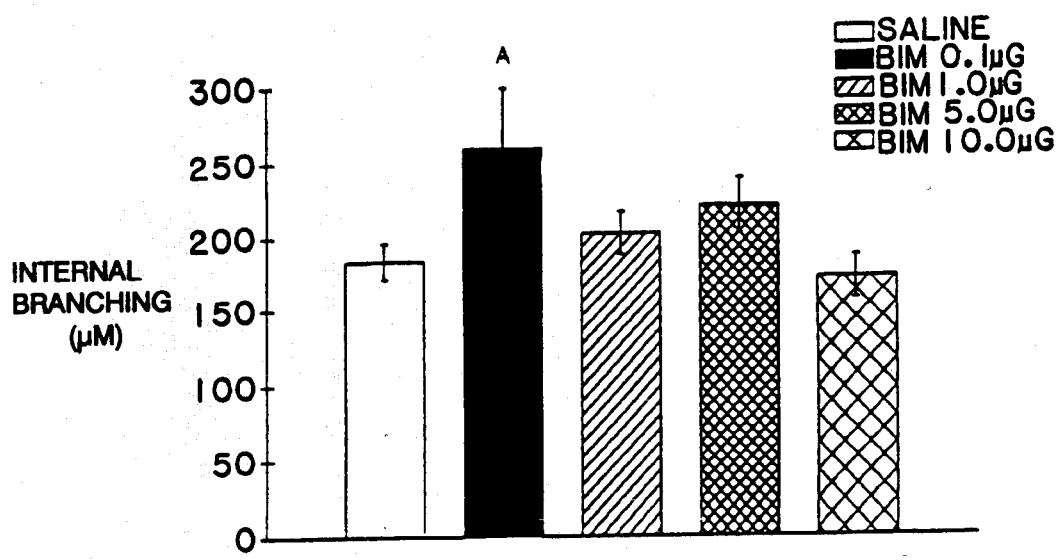
FIG. 6  A: p<0.025
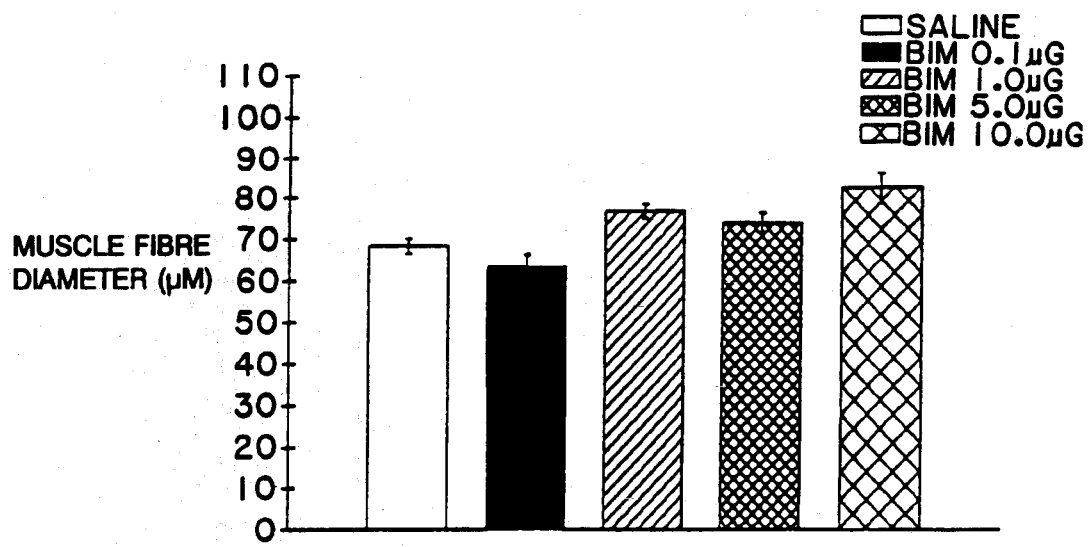
FIG. 7  •p<0.05

PEPTIDES AIDING NERVE REGENERATION

This invention was made in the course of work under a grant of award from the U.S. government; therefore, the U.S. government has rights in the invention.

BACKGROUND OF THE INVENTION

This application is a continuation-in-part of pending U.S. Ser. No. 07/431,339 filed Nov. 3, 1989, now abandoned, which is a continuation-in-part of U.S. Ser. No. 728,847 filed Apr. 30, 1985.

This invention relates to therapeutic peptides.

ACTH-like neuropeptides can facilitate nerve regeneration in the central and peripheral nervous systems. Bijlsma et al. *Eur. J. Pharm.*, 76 (1981) 73–79 and Bijlsma et al. *Eur. J. Pharm.*, 92 (1983) 231–236 describe using ACTH-like neuropeptides, including H—Met($O_2$)—Glu—His—Phe—D—Lys—Phe—OH and α-MSH, to restore sensorimotor function in rats having crushed sciatic nerves (where no D- or L-isomeric designation is given herein, the naturally occurring L-isomer is intended).

SUMMARY OF THE INVENTION

In general, the invention features a heptapeptide useful for regenerating sensory or motor nerves, of the formula:

$A^1$—$A^2$—$A^3$—$A^4$—Phe—Arg—Trp—$A_5$, wherein $A^1$ is H or acetyl; $A^2$ is Ala, D—Ala, Nle, or Met; $A^3$ is Glu or Gln; $A^4$ is His or Tyr, $A^5$ is $NH_2$, Gly—$NH_2$, or D—Ala—$NH_2$, provided that when $A^3$ is Glu and $A^4$ is His, $A^2$ cannot be Met or Nle; or a pharmaceutically acceptable salt thereof.

In preferred embodiments of the heptapeptide, $A^1$ is H, $A^2$ is Nle, $A^3$ is Gln, $A^4$ is His, and $A^5$ is Gly—$NH_2$; $A^1$ is H, $A^2$ is Nle, $A^3$ is Glu, $A^4$ is Tyr, and $A^5$ is Gly—$NH_2$; $A^1$ is H, $A^2$ is Met, $A^3$ is Gln, $A^4$ is Tyr, and $A^5$ is Gly—$NH_2$; $A^1$ is H, $A^2$ is Ala, $A^3$ is Gln, $A^4$ is Tyr, and $A^5$ is Gly—$NH_2$; and $A^1$ is H, $A^2$ is D—Als, $A^3$ is Gln, $A^4$ is Tyr, and $A^5$ is Gly—$NH_2$.

In other preferred embodiments, a therapeutically effective amount of the therapeutic heptapeptide and a pharmaceutically acceptable carrier substance, e.g., magnesium carbonate or lactose, together form a therapeutic composition for aiding in regenerating nerves of the peripheral nervous system and the brain. The composition can be in the form of a pill, tablet, capsule, liquid, or sustained release tablet for oral administration; a liquid for nasal administration; or a liquid for intravenous, subcutaneous, a topical, transdermal, or sustained release tablet, surgical suture, glue, or chamber for parenteral, or intraperitoneal administration.

The invention also features a method for treating muscle wasting which results from motor nerve trauma (e.g., severed or compressed motor nerves) or a genetic disease that causes neuromuscular degeneration, the method including the step of administering to a mammal, particularly a human patient, an amount of any one of the heptapeptides of the generic formula sufficient to preserve the muscle mass in the absence of motor neuron function.

In preferred embodiments, the heptapeptide has the following formula: $A^1$ is H, $A^2$ is D—Ala, $A^3$ is Gln, $A^4$ is Tyr, and $A^5$ is Gly—$NH_2$; and the disease may be Duchenne muscular dystrophy.

The method is useful for treating chronic, degenerative neuromuscular diseases, such as Duchenne muscular dystrophy, or for treating or preventing muscle degeneration resulting from nerve trauma, i.e., from crushed or severed nerves, or nerve trauma resulting from toxic or metabolic (e.g., diabetes or cancer).

Other features and advantages of the invention will be apparent from the following description of the preferred embodiments thereof, and from the claims.

DESCRIPTION OF THE PREFERRED EMBODIMENTS

We first briefly describe the drawings.

FIG. 1 shows a schematic illustration of gait differences for different injuries, and is taken from Bain et al., 1989 Plastic and Reconstructive Surgery.83:129.

FIG. 2 is a line graph of the functional recovery after treatment with saline or different dosages of BIM 22015 (100%=100% recovery; data in mean and its SEM).

FIG. 3 is a bar graph representation of the walking test (SEM is adjusted by the 95% confidence multiplier).

FIG. 4 is an endplate area bar graph.

FIG. 5 is an endplate perimeter graph ($p < 0.025$).

FIG. 6 is an endplate graph of internal branching,

FIG. 7 is an endplate muscle fiber diameter ($p < 0.05$),

We now describe the structure, synthesis, testing, and use of preferred embodiments of the invention.

Structure

The heptapeptides of the invention have the general formula recited in the Summary of the Invention above. They all have an $NH_2$ at the carboxy terminal end, in addition to Phe at position 4, Arg at position 5, and Trp at position 6.

The heptapeptides can be provided in the form of pharmaceutically acceptable salts. Examples of preferred salts are those of therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as hydrohalic acids, e.g., hydrochloric acid, sulfuric acid, or phosphoric acid.

Synthesis

The synthesis of H—Nle—Gln—His—Phe—Arg—Trp—Gly—$NH_2$ follows.

Other heptapeptides of the invention can be prepared by making appropriate modifications of the following synthetic method.

The first step is the preparation of Nle—Gln—His—Phe—Arg—Trp—Gly-benzhydrylamine-resin, as follows.

Benzyhydrylamine-polystyrene resin (Bachem, Inc.) (1.00 g, 0.5 mmole) in the chloride ion form is placed in the reaction vessel of a Beckman 990B peptide synthesizer programmed to perform the following reaction cycle: (a) $CH_2Cl_2$; (b) 33% trifluoroacetic acid $CH_2Cl_2$ (2 times for 1 and 25 min. each); (c) $CH_2Cl_2$; (d) ethanol; (e) $CH_2Cl_2$; (f) 10% triethylamine in $CHCl_3$; and (g) $CH_2Cl_2$.

The neutralized resin is stirred with Boc-glycine and diisopropylcarbodiimide (1.5 mmole) in $CH_2Cl_2$ for 1 hour and the resulting amino acid resin is then cycled through steps (a) to (g) in the above wash program. The following amino acids (1.5 mmole) are then coupled successively by the same procedure:Boc—Trp, Boc—tosyl—Arg, Boc—Phe, Boc—carbenzoxy—His, Boc—Gln, and Boc—Nle.

After washing and drying, the completed resin weighs 1.60 g.

From the above resin prepared H—Nle—Gln—His—Phe—Arg—Trp—Gly—NH$_2$, as follows.

A mixture of the above heptapeptide resin (1.85 g, 0.5 mmole) and a solution of 4 ml anisole, and 36 ml hydrogen fluoride is stirred at 0° C. for 45 minutes. Excess hydrogen fluoride is evaporated rapidly under a stream of dry nitrogen, after which the free peptide is precipitated and washed with ether.

The peptide is then dissolved in a minimum volume of 50% acetic acid and eluted on a column (2.5×100 mm) of Sephadex G-25. Fractions containing a major component, as determined by u.v. absorption and thin layer chromatography (tlc) are pooled and evaporated to a small volume in vacuo. This solution is applied to a column (2.5×50 cm) of octadecylsilanesilica (Whatman LRP-1, 15–20 m mesh size) which is eluted With a linear gradient of 0–40% acetonitrile in 20% acetic acid in water. Fractions are examined by tlc and analytical high performance liquid chromatography (hplc) and pooled to give maximum purity. Repeated lyophilization of the solution from water gives 81 μg of the product as a white, fluffy powder.

This material is found to be homogeneous by hplc and tlc. Amino acid analysis of an acid hydrolysate confirms the composition of the heptapeptide.

H—Nle—Glu—Tyr—Phe—Arg—Trp—Gly—NH$_2$,
H—Met—Gln—Tyr—Phe—Arg—Trp—Gly—NH$_2$,
H—Ala—Gln—Tyr—Phe—Arg—Trp—Gly—NH$_2$, and
H—D—Ala—Gln—Tyr—Phe—Arg—Trp—Gly—NH$_2$ are prepared in similar yields in an analogous fashion by appropriately modifying the above procedure.

Testing of Heptapeptides

Heptapeptides of the invention may be testing for their effect on nerve and muscle degeneration as described below.

One heptapeptide of the invention, BIM-22015, which has the amino acid formula D—Ala—Gln—Tyr—Phe—Arg—Trp—Gly—NH$_2$, was tested on two different types of peripheral nerve lesions: crushed and sectioned nerves. In rats, the effect of different dosages and modes of administration of BIM-22015 on regeneration of the crushed peroneal nerve or the sectioned sciatic nerve was investigated. In rabbits, morphological studies were performed in which the sciatic nerve was sectioned and sutured prior to treatment with BIM-22015. The results of these combined studies, presented below, suggest that BIM-22015 may be more effective on the neuromuscular junction (i.e., endplate) than on the axon.

Effect of BIM-22015 on Crushed Peroneal Nerve Regeneration in Rats

The effect of BIM-22015 regeneration of the crushed peroneal nerve in the rat was assessed using both morphological and physiological studies, as follows. Both locomotor pattern and endplate morphology during the early stages of crushed nerve regeneration were assessed after treatment with BIM-220150 Adult Sprague-Dawley male rats (Taconic Farms) were maintained at 25° C. on a 12 hour light and a 12 hour dark cycle and were supplied with standard rat chow and water ad lib. All surgery was performed under anesthesia with 8% chlorohydrate (0.6 ml/100 g I.P.). Denervation was accomplished using a #5 Dumont forceps with a uniformly filed tip to crush the peroneal nerve. This crush produced a 1 mm wide lesion just proximal to the EDL (extention digitarum longus) muscle. The wound was closed with surgical staples. Following surgery, the animal was immediately administered saline or BIM-22015 in one of the following dosages: (1) 0.9% saline, (2) 10.0 ug BIM-22015, (3) 5.0 ug BIM-22015, (3) 1.0 ug BIM-22015, or (4) 0.1 ug BIM-22015 (per animal). Administration continued once every 48 hours for 5 days; on day 5, the rats were killed and tissues taken for morphological analysis. All injections and surgeries occurred between 10:00 and 12:00 noon.

Locomotor pattern was tested by measuring the walking pattern of the animal. The animal was allowed to walk up a 20° inclined platform. The track was well-lit by fluorescent tubes and a dark box was placed at the end of the track. This dark and light differences was used to entice the animal to walk up the track. The track was lined with 13.5 inch wide continuous computer paper (20 lb.). The rat's hind feet were dipped in non-toxic ink, and the animal allowed to walk naturally. The walking pattern test was performed the day prior to surgery and on the 3rd, 4th, and 5th days after surgery. All walking tests were performed between 10:00 and 12:00 noon. Six undisturbed and consistent walking patterns were chosen for analysis of toespread differences. FIG. 1 is a schematic illustration of the possible patterns. The distance between the first and fifth digit was determined using a Manostat mechanical caliper (type 6911) with accuracy of ±0.005 mm0 The contralateral foot was used as a control to negate the size differences in individual animals. The Student T test was used to determine the statistical differences, and data were expressed as means of the six sharpest toespreads and the standard error of the mean (using 95% confidence formula), standard deviation, and variances.

Although the results show no statistical significance in any of the parameters measured, probably due to the small animal number per group and the small magnitude of treatment-related improvement, the 0.1 μg dosage of BIM-22015 resulted in a very consistent upward recovery rate. These results, presented in FIGS. 2 and 3, show that the optimal dosage of the BIM-22015 analog is 0.1 μg. The other dosages outperformed the saline control animal but only by a slight margin. The 0.1 μg dosage slightly outperformed the 50 μg. These results illustrate the beneficial effect of BIM-22015 on the recovery rate of locomotion at the lowest dose tested (0.1 ug).

Morphology

Morphological studies of crushed nerve regeneration were performed as follows. On day 5, the rats were anesthetized with 8% chlorohydrate (0.6 ml/100 g IP) before surgery. The animal was placed ventral side down and a skin incision was made on the hindlimb from the lateral epicondyle of the femur to the lateral malleolus in the ankle. The extensor digitorium longus muscle (EDL) was then carefully exposed from its surrounding connective tissue and extreme care taken to preserve the blood supply. The EDL is a heterogenous muscle consisting of both fast white muscle fibers and slow red muscle fibers. It is classified as a fast muscle based upon its isometric twitch parameters. The origin of the EDL is the epicondyle of the femur to the distal tendon which divides into four parts with insertions into the third phalange base of the second to the fifth digits. It is innervated by the peroneal nerve and its blood is supplied by the anterior tibial artery. The muscle was prepared for staining as follows.

The silver-cholinesterase method of staining of Pecot-Dechavssine et al. (1979 Stain. Technol. 54:25) was used to stain the endplates, or neuromuscular junctions, of the EDL. Briefly, the muscle was fixed in situ by 1% neutral formalin in normal Ringer's solution. The muscle was then excised and placed in fresh 1% neutral formalin solution for extra 3–4 minutes. The endplates were localized with the stain described by Karnovsky et al. (1964, J. Hist. Chem. Cytochem. 12:219) for 7–15 minutes under visual control. After localization, the EDL was soaked in 5% neutral formalin solution for 20 minutes, then washed in Triton X-100 detergent for 1 hour. After the detergent step, the EDL was fixed in 80% ethanol solution for 1 hour. Finally, the endplates were impregnated with silver using 0.5% protargol solution overnight (12–30 hrs., at 37° C.).

The following day, the excess silver was reduced using a Bodian developer for 18 minutes. The muscle was rinsed in distilled water, finely teased, and mounted using a glycoglyerol mounting gel.

The endplates were observed using Olympus BH series binocular microscope at a magnification of 100× using an oil immersion objective lens. A low light sensitive video camera mounted on top of the Olympus projected the slide onto a black and white monitor. A Bioquant image digitizer with a manual optic mouse was used to determine the following parameters: (1) endplate parameter, (2) endplate area, (3) endplate internal branching, and (4) muscle fiber diameter. The Bioquant statistical package was used to determine statistical differences, and the data are expressed as means and standard error of the mean. The Student's t-test and the ANOVA statistical tests were performed. The Bioquant image digitizer was attached to a Hipad Digitizing pad (Houston Instruments, Austin, Tex.) and was linked to the Apple IIe personal computer using a morphometry software, Bioquant II (R & M Biometrics, Nashville, Tenn.).

Results

Treatment of the crushed nerve with BIM-22015 results in a compensatory effect at the neuromuscular junction which was most evident at the lowest dose administered (0.1 µg). The results showed a significant increase in endplate perimeter at 0.1 µg ($p<0.025$) (FIGS. 4 and 5) and 5.0 µg ($p<0.05$) of BIM-22015, and internal branching (FIG. 6 and Table 1) at 0.1 µg BIM-22015 ($p<0.025$). Measurement of the endplate muscle fiber diameter revealed a significant ($p<0.005$) high muscle hypertrophy at two dosages of BIM 22015, 1.0 µg and 10.0 µg (FIG. 7). At the 0.1 µg and 10 µg doses, there was also a dose-effect relationship, which may be due to enhancement of muscle-sparing effects similar to the one observed with some peptides, such as MSH and β-endorphin. Hugh et al. (1989, Neuroscience Letts. 103:169) have shown endplate over-expression of α-MSH and β-endorphin in animals suffering from motoneurone disease, e.g., in wobbler or dystrophic mice.

Effect of BIM-22015 on Muscle Weight After Sciatic Nerve Section in Rats

BIM-22015 was tested for its effect on muscle weight after sciatic nerve section, and rejoining as follows. Four groups of between eight and ten Wistar rats, eight weeks of age and approximately 200 g each, were tested. The sciatic nerve of each rat was dissected and a clean section was performed with surgical scissors. The proximal and distal stumps were then glued together with tissucol, and BIM-22015 was administered topically in surgical glue (i.e., tissucol) at 100 ug/0.5ml (group 2), at 1.1 ug/0.5ml (group 3), or by s.c. administration at 5ug.kg.day for 18 days. The control group (group 1) was treated with tissucol alone. The sectioned nerve was allowed to regenerate for 35 days before evaluation.

On day 35, each rat was anesthetized with phenobarbital prior to surgery. The exterior leg was surgically opened in order to free the common extensor muscle of the finger. The distal tendon was cut at the level of the heel. Following electrophysiological measurements of muscle tension in response to acute stimulus, muscle tentanos at 100 Hz, muscle exhaustion following a 5 second contraction at 500 Hz, the muscle was sectioned at the proximal level, the tendons removed, and the muscle was dried and weighed.

Table 2 shows results of muscle measurements. The results show a dependence on the route of administration of BIM-22015, as topical administration (groups 2 and 3) was largely ineffective, but the s.c. route of administration (group 4) was associated with significant improvement of muscle strength. For example, when muscle weight is normalized to mean animal weight (Table 2, column 2), group 4 (s.c. administration) showed an improvement of 15% over the control group 1, but groups 2 and 3 showed little improvement. The increase of muscle weight by s.c. administration of BIM-22015 may be due to an increase in the number of fibers which are innervated or in the volume of a few reinnervated fibers. It was also determined that the increase in muscle weight was not associated with edema or lipid infiltration. The inter-animal variability in this experiment was too large to achieve statistical significance.

The effect of BIM-22015 on muscle strength is shown in Tables 3 and 4. Group 4 (Table 3) shows a significant ($p=0.01$) improvement of 30% over control group 1 (column 2, Table 3). This improvement is also evident when the muscle strength (i.e., contractile response) is normalized to the muscle weight (column 3, Table 3). Group 4 (Table 4) shows an improvement of 28% ($p=0.05$) over control group 1 (column 1, Table 4). However, when muscle strength is normalized to muscle weight (column 2), the improvement is no longer significant compared to the control group. Table 4 also shows that the speed of muscle contraction (column 3) is dramatically improved (300%) in group 4 compared to group 1; this difference is statistically significant ($p=0.01$). The speed of relaxation (column 4, Table 4) is also dramatically improved in group 5 compared to group 1. However, no effect was found on fatigability of the muscle at both low (100 Hz) and high (500 Hz) frequency.

The morphological results show an increase in muscle weight after s.c. administration of BIM-22015, which can only be accounted for by an increase in the contractile protein from the muscle fiber. The results of the functional tests suggest that muscle reinnervation was accelerated by treatment with BIM-22015. These results confirm the conclusion that BIM-22015 prevents muscle wasting, as was found above for experiments involving crushed peroneal nerve regeneration.

Morpohological Studies of the Effect of BIM-22015 After Section and Suture of Sciatic Nerve in Rabbits The sciatic nerve of the rabbit after transection followed by end-to-end suture was studied, using light and transmission electron microscopy. The effects of BIM-22015 on the number of newly formed myelinated nerve fibres, the axonal diameter, and the thickness of the myelin sheath were examined, as follows.

Preparation of Nerve Samples 52 young, adult male rabbits of the White New Zealand strain were anesthetised under sterile conditions with sodium pentobarbital injected into the marginal ear vein in a dose of 30 µg/kg body weight. A neurosurgeon performed a transection of the left sciatic nerve followed by a neurosuture under the operating microscope. A lateral skin incision was made on the thigh between the trochanter major and the knee joint. The thigh musculature was exposed to reveal the nerve which was then transected at a point about 1.5 cm distal to where it emerged from below the gluteal muscle. The point of transection was located distal to its division into the muscular branch of the sciatic nerve. By preserving this branch of the nerve, the animals showed virtually no signs of paralysis after the operation. The two ends of the nerve could be fixed by two to three tension-free sutures around the peri- and epineurium. The wound was closed by a continuous skin suture and no antibiotics were used. Daily administration of BIM-22015 to 25 animals began one hour after the start of the operation. The animals received the substance subcutaneously in a dose of 1 µg/kg bodyweight per day in 1 ml sodium chloride solution. After the operation, the rabbits were divided into 4 groups each of 12 animals (except Group 4 had 16 animals). One-half of each group (6 animals, except for 7 animals in Group 4) was treated with BIM-22015 (Test animals) and the remaining animals were given a sodium chloride solution (Control animals).

After sacrifice of the animals under Nembutal anesthesia the left sciatic nerve was removed from each of 6 test animals and 6 control animals after 3, 8 or 32 days, and from 7 test and 9 control rabbits after 96 days. In each case, an approximately 4 cm piece of the nerve could be obtained. Immediately after its removal, the nerve was stretched and stuck to a Styropor frame and placed in a 5% cooled (4° C.) cacodylate buffered glutaraldehyde solution (pH 7.2) for 1–2 hours.

After a two to three hour pre-fixation, tissue blocks were removed from the following regions: the area of the transection, 4 mm proximal and 3, 6 and 10 mm distal to this point. The main areas of interest for investigating changes were to be the region of the transection and 1 cm distal to this. The samples obtained were fixed for another 24 hours in special glass vessels with cacodylate buffered, cooled (4° C.) glutaraldehyde solution. The samples were then rinsed for 1–3 hours in cacodylate buffer (pH 7.2) and then postfixed in 1% osmium tetroxide for 2 hours. After repeated rinsing with cacodylate buffer (4×30 minutes) and dehydration in graded alcohol solutions up to an alcohol concentration of 100% (in each case for 30 minutes), the samples were placed for 60 minutes in propylene oxide and then in a propylene oxide-Epon 812 mixture (proportion 1:1). The samples were then transferred to pure Epon 812 (Serra, Heidelberg) for embedding. The polymerisation of the plastic medium took place in a special polymerisation cupboard for one day each at 35° C. and 45° C. and for three days at 60° C..

With an ultramicrotome 0.5 µm thick semithin sections were cut. The sections were then stained with 0.25% toluidine blue at 80° C. and used for evaluation of the tissue changes by light microscopy and the subsequent preparation of ultrathin sections. The latter were obtained using an ultramicrotome (Reicherr OM U3) and placed on copper-mesh microscope slides. The contrast process was carried out in two steps in the automatic contrast machine (2168 Ultrastainer Carlsberg System, LKB Sweden). In the first step, a 30 minute treatment with Ultrastain 1 (uranyl acetate solution) was carried out at 40° C., followed by a washing process and, finally, a counter-contrast was undertaken for 80 seconds with Ultrastain 2 (lead citrate solution). The ultrastructural evaluation was undertaken with the electron microscope EM (Zeiss, Oberkochen) at 60 kV. The results were documented on dimensionally-stable film material.

Sensorimotor Function Test

Female, Sprague-Dawley rats (Charles River Breeding Labs) were used at an age of 7–8 weeks (120–140 g). Under ether anesthesia, the right sciatic nerve was carefully exposed and crushed with constant pressure, hemostatic forceps for 30 sec prior to closure and suturing of the incision. After surgery, the animals were randomly assigned to treatment groups of 10.

The test peptides were administered s.c. in 0.9% NaCl in a vol of 0.1 ml. NaCl (0.9%) served as the control. Injections were started immediately after surgery and given every 24 hr thereafter for approximately 20–25 days.

The criterion of sciatic nerve regeneration was based on the recovery of the foot-flick response to thermal pain. Beginning 48 hr after surgery, the rats were tested five days a week for the ability to withdraw, from a heat source, the paw innervated by the crushed nerve. All sensorimotor testing was performed between 1:00 and 3:00 p.m. Specifically, the rat was immobilized by wrapping in a towel, and the sole of the lesioned limb was placed over the aperture of a modified d'Amour apparatus. The time required to withdraw the foot was recorded to the nearest 0.1 of sec using a digital stopwatch. If no response occurred by 5 sec, the test was terminated to avoid tissue damage. The observe measuring the foot-flick response was blind to the treatment group being tested. All animals were acclimatized to the testing procedure prior to surgery. Baseline values were obtained by determining the response time for the unlesioned limb.

Image Analysis

In order to analyze the influence of BIM 22015 on the morphology of myelinated nerve fibres during regeneration, a computer-controlled semi-automatic interactive image analysis was carried out. With this method, geometric data were collected and evaluated. The system used consists of a coordinates measuring table with a processor for measuring geometric parameters and an electronic pencil (MOP AM 02 KONTRON, Eching) with a computer (HP 9845 B, Hewlett-Packard) to take data from MOP AM 02 and transform it from geometric sizes into the desired parameters using a special program.

The measurements were carried out on electron micrographs with a magnification of 6,400. At this magnification, the structures were large and clear enough to be able to trace them exactly with the electronic pencil. In addition, at this magnification, a sufficiently large number of nerve fibres were portrayed, so that the amount of material in the micrograph remained within a certain range.

The morphometric measurements were taken on image material from 6 test and control animals with a survival time of 32 days and 7 test and 9 control animals with a survival time of 96 days. 10 micrographs each from the region of the operation site (loc 2) and from a region 1 cm distal from this site (loc 5) were chosen at random.

The outer and the inner perimeters of the myelin sheath and the external perimeter of the axon were traced with the electronic pencil. In the majority of cases this is identical with the inner perimeter of the myelin sheath. The MOP AM 02 measured the following geometric data: the total area of the nerve fibre, i.e., the area of the axon and the myelin sheath, the area of the axon, the external perimeter and the outer shape of the nerve fibre, and the inner perimeter of the myelin sheath and the shape of the axon in cross-section. From these values, a computer program calculated the thickness of the myelin sheath and the diameter of the axon as diameter of a circle of equal area. As the third variable, the program determined a form factor, that gave the deviation from circularity.

In the next step, the individual values of all test and control animals were collated separately for the variables; myelin sheath thickness and axon diameter per localisation and time point, and the distribution of the individual values within the treated and untreated animals determined. A second statistics program provided the mean value, the standard deviation and minimal and maximal values for each variable within a group of animals according to localisation and time point. Finally, histograms could be were prepared with these data that represented the data in graphical form.

Analysis of Variance

All the individual values of the two variables, myelin sheath thickness and axon diameter per animal, localisation and time point were first converted separately to logarithms. The mean value was calculated from these new values, and then converted back to ordinary numbers. The two-way analysis of variance could be carried out with the resulting representative values using the statistics program ANOVA (NVA2U). The aim of this analysis of variance was to show what effect the factor time and the factor treatment have on the growth of the myelin sheath and the axon. In addition, the time-dependency of the effect was investigated.

Results

The light microscopic evaluation of the semi-thin sections of 0.5 μm following the surgical severance and microsurgical end-to-end suture of the sciatic nerve did not disclose definite differences between the control and experimental groups. The light microscopically demonstrable effects of the treatment with BIM-22015 cannot be confirmed due to the great variation of findings among the animals. Since the sciatic nerve is not very long in the rabbit and therefore only permits the evaluation of a localisation 10 mm distal from the surgical site, it is very difficult to estimate the speed of the growing nerve. The nerve grows 1.2 to 1.4 mm per day so that numerous nerve fibres have already reached the localisation 10 mm distal from the surgical site by day 8 p.o. In addition, differences between control and experimental animals were not observed by electron microscopy.

The morphometric findings in the region of transection and in the region 1 cm distal to the transection are summarized in Table 5 and Table 6, respectively.

The myelinated fibres could only be seen after 8 days with electron microscopy, because the myelin sheaths were still very thin. However, they were so few in number that no statistical evaluation could be made at this time. This finding confirms the observation of Gutman et al. (1943, J.Physiol. 101:489), that the regeneration of peripheral nerve fibres after crushing occurs faster than after a nerve transection. Since in the early regeneration phase (3 and 8 days after surgery), remyelinisation is not yet very far advanced, the number of nerve fibres, the axon diameter and the myelin sheath thickness were analyzed statistically at a time when the myelinated fibres seen on light microscopy were present in larger numbers (32 and 96 days after the operation).

In the region of the transection, the differences between treated and untreated animals were not confirmed statistically, although the myelin sheath is, on average, thicker in the treated animals both after 32 days and after 96 days. In the region 1 cm distal of the transection, the myelin sheath is also only slightly thicker in the treated animals after 32 days than in the untreated controls. In the period from the 32nd to the 96th day, the myelin sheath grows almost twice as fast in the treated animals. After 96 days, the myelin sheath in the treated animals is significantly thicker than in the controls. Thus the effect of BIM-22015 on the increase in thickness of the myelin sheath over the period from the 32nd to the 96th day is statistically confirmed. A statistically significant effect of BIM-22015 on the axon diameter could not be demonstrated either on the 32nd or on the 96th day p.op. Although also not statistically confirmed, on average, a higher number of myelinated nerve fibres could be counted in the treated animals. After 32 days, the number of medullated fibres was considerably higher in the region of the transection, and in the area 1 cm distal of the lesion, both after 32 and 96 days. The fact that these differences were not statistically significant is probably due to the large scatter of the individual values in the groups of both treated and untreated animals. These results should not be ignored in evaluating the effect of BIM 22015 on the regeneration of peripheral nerves.

The macroscopically observed thickening in the region of the transection due to the formation of granulation tissue in two control animals is to be regarded in both cases as a random result and independent of the effect of BIM 22015 treatment. Overall, the formation of granulation tissue after the operation was so small that it did not affect the nerve regeneration.

TABLE 1

Endplate Morphology

| Treatment | Area (SEM) | Perimeter | Internal Branching | Muscle Fiber Diameter |
|---|---|---|---|---|
| Saline | 3434.7(223.7) | 220.9(6.27) | 183.5(12.1) | 68.3(1.88) |
| BIM 0.1 μG | 3562.6(179.3) | 244.3(8.63)A | 260.5(39.2)A | 63.6(2.72) |
| BIM 1.0 μG | 3671.9(174.7) | 231.7(5.22) | 201.6(14.2) | 76.9(1.70)C |
| BIM 5.0 μG | 2967.9(164.9) | 204.2(5.98)B | 220.2(18.7) | 74.2(2.35) |
| BIM 10.0 μG | 4022.8(442.2) | 231.7(12.2) | 173.2(14.6) | 82.8(3.74)C |

A = p < 0.025

TABLE 1-continued

Endplate Morphology

| Treatment | Area (SEM) | Perimeter | Internal Branching | Muscle Fiber Diameter |
|---|---|---|---|---|
| B = p < 0.050 | | | | |
| C = p < 0.005 | | | | |

TABLE 2

| | Animal Weight 35d. p.o. (g) | Normalized to Mean Animal Weight | Muscle Weight 35d. p.o. (µg) |
|---|---|---|---|
| Group 1 Control | 317.7 ±13.0 n = 9 | 0.198 | 63.1 ±13.0 n = 8 |
| Group 2 Tissue col 10.0 µg/0.5 ml | 321.0 ±16.6 n = 10 | 0.211 | 67.9 ±7.0 n = 10 |
| Group 3 Tissue col 1.1 µg/10.5 ml | 280.5 ±23.4 n = 10 | 0.212 | 59.7 ±7.3 n = 9 |
| Group 4 s.c. 5 µg 1 kg/day | 322.5 ±16.7 n = 8 | 0.226 | 73.1 ±7.5 n = 8 |

TABLE 5

Morphometric Findings in the Region of the Transection
Mean values of myelin sheath thickness (µm)

| Days p.op. | Test Animals | Control Animals |
|---|---|---|
| 32 | 0.398 | 0.352 |
| 96 | 0.551 | 0.523 |
| Mean values of axon diameter (µm) | | |
| 32 | 1.888 | 2.241 |
| 96 | 2.335 | 2.498 |
| Number of myelinated axons/0.004 sq. mm | | |
| 32 | 78 | 63 |
| 96 | 62 | 64 |

TABLE 3

Characteristics of Muscle Tetnus
of the common extensor muscle of the fingers, 35d. p.o.p

| | Muscle Strength (g) | Muscle Strength Normalized to Muscle Weight (g/ug) | Speed of Contraction (g/ms) | Speed of Relaxation (g/ms) | Tetanic Strength/ Single Pulse Strength (%) | Fatigue (%) |
|---|---|---|---|---|---|---|
| Group 1 n = 8 | 71,12 ±20,27 | 1,08 ±0,31 | 3098 ±1685 | 1573 ±1103 | 351,25 ±82,45 | 72,75 ±13,85 |
| Group 2 n = 10 | 61,83 ±17,03 | 0,91 ±0,16 | 2409 ±1174 | 2034 ±1612 | 307,50 ±35,11 | 73,80 ±15,75 |
| Group 3 n = 9 | 51,55 ±19,91 | 0,84 ±0,26 | 1737 ±1059 | 884 ±551 | 343,00 ±67,50 | 75,55 ±14,39 |
| Group 4 n = 8 | 91,77 ±12,15 | 1,26 ±0,10 | 5507 ±1116 | 4226 ±1335 | 347,12 ±26,72 | 72,12 ±7,82 |

TABLE 4

Characteristics of a Single Pulse
of the common extensor muscle of the finger, 35d. p.o.p.

| | Latence (ms) | Strength (g) | Muscle Strength Normalized to Muscle Weight (g/ug) | Contraction Time (ms) | Half-Relaxation Time (ms) | Speed of Contraction (g/ms) | Speed of Relaxation (g/ms) |
|---|---|---|---|---|---|---|---|
| Group 1 n = 8 | 9.48 ±0.88 | 20.30 ±4.42 | 0.30 ±0.09 | 28.65 ±6..18 | 63.02 ±9.54 | 2562 ±1289 | 585 ±231 |
| Group 2 n = 10 | 9.93 ±1.29 | 20.03 ±4.48 | 0.30 ±0.06 | 28.86 ±4.73 | 64.69 ±10.56 | 2419 ±776 | 514 ±191 |
| Group 3 n = 9 | 7.65 ±0.75 | 14.96 ±5.06 | 0.25 ±0.07 | 16.37 ±1.86 | 40.93 ±5.34 | 2939 ±1129 | 593 ±200 |
| Group 4 n = 8 | 9.48 ±0.76 | 26.45 ±3.43 | 0.37 ±0.04 | 27.68 ±3.78 | 60.72 ±8.41 | 2420 ±848 | 635 ±183 |

TABLE 6

| | Morphometric results in the region 1 cm distal to the transection | |
|---|---|---|
| | Mean values of myelin sheath thickness (μm) | |
| Days p.op. | Test Animals | Control Animals |
| 32 | 0.310 | 0.298 |
| 96 | 0.600 | 0.532 |
| | Mean values of axon diameter (μm) | |
| 32 | 1.545 | 1.601 |
| 96 | 2.078 | 1.887 |
| | Number of myelinated axons/0.004 sq. mm | |
| 32 | 64 | 43 |
| 96 | 85 | 67 |

Therefore, BIM-22015 exerts an effect not only in the early regeneration phase, but also at later times after nerve trauma, with both the number of axonal sprouts and also remyelinisation and thickness of the myelin sheath being affected.

The results of the sensorimotor function test are shown in the attached table.

| SCIATIC NERVE REGENERATION ASSAY - μG/24 HRS | |
|---|---|
| Peptide | % Reduction of Recovery Time |
| BIM-22015<br>D—Ala—Gln—Tyr—Phe—Arg—Trp—Gly—NH$_2$ | 28 |
| BIM-22016<br>L—Ala—Gln—Tyr—Phe—Arg—Trp—Gly—NH$_2$ | 13 |
| BIM-22010<br>NLeu—Gln—His—Phe—Arg—Trp—Gly—NH$_2$ | 13 |
| BIM-22013<br>NLeu—Gln—Tyr—Phe—Arg—Trp—Gly—NH$_2$ | 0 |

Use

When administered to a mammal (e.g., orally, topically, transdermally, intravenously, parenterally, nasally, or by suppository), the heptapeptides are effective in aiding in regenerating nerves of the peripheral and central nervous systems following nerve damage, and in preventing muscle degeneration or increasing muscle mass. The heptapeptides are administered beginning directly following the injury, for a period of ten days or more. Administration is daily or every other day.

The heptapeptides of the invention can be used to treat nerve crush lesions and neuropathies of alcoholic, diabetic, or toxic substance exposure origins. The heptapeptides can also be used to aid in suturing severed nerves. The heptapeptides can promote the growth of new nerve processes, enhance the connection of nerves to muscles, and prevents muscle wasting. Where the heptapeptides are used to treat nerve trauma, an initial dose may be administered immediately after nerve injury, and a second dose at a later time, e.g., two weeks, at a higher dose to preserve the muscle mass. Where muscle degeneration has already occurred, such as in degenerative neuromuscular disease, the heptapeptides may be administered at intervals, e.g., daily or weekly, and dosages sufficient to cause muscle hypertrophy.

The heptapeptides can be administered to a patient in a dosage of 1 μg/kg/day to 250 μg/kg/day, preferably 5–100 μg/kg/day.

Other embodiments are within the following claims.

We claim:

1. A peptide of the formula:

$$A^1—A^2—A^3—A^4—Phe—Arg—Trp—A^5$$

wherein $A^1$ is H or acetyl;

$A^2$ is D—Ala;

$A^3$ is Glu or Gln; and $A^4$ is His or Tyr;

$A^5$ is Gly—NH$_2$; or a pharmaceutically acceptable salt thereof.

2. The peptide of claim 1, wherein $A^1$ is H; $A^3$ is Gln; $A^4$ is Tyr; and $A^5$ is Gly—NH$_2$; or a pharmaceutically acceptable salt thereof.

3. The peptide of claim 1, wherein $A^1$ is H; $A^2$ is D—Ala, $A^3$ is Gln; $A^4$ is Tyr; and $A^5$ is Gly—NH$_2$; or a pharmaceutically acceptable salt thereof.

4. The peptide of claim 1, wherein $A^3$ is Gln; or a pharmaceutically acceptable salt thereof.

5. The peptide of claim 1, wherein $A^4$ is Tyr; or a pharmaceutically acceptable salt thereof.

6. The peptide of claim 1, wherein $A^3$ is Gln and $A^4$ is Tyr; or a pharmaceutically acceptable salt thereof.

7. The peptide of claim 1, wherein $A^1$ is H.

8. The peptide of claim 4, wherein $A^1$ is H.

9. The peptide of claim 5, wherein $A^1$ is H.

10. The peptide of claim 6, wherein $A^1$ is H.

11. A composition comprising a therapeutically effective amount of the peptide of claim 1 together with a pharmaceutically acceptable carrier substance.

12. The composition of claim 11, wherein said composition is in the form of a liquid capable of being administered intravenously, subcutaneously, parenterally, or intraperitoneally to a patient in need of said peptide.

* * * * *

UNITED STATES PATENT AND TRADEMARK OFFICE
CERTIFICATE OF CORRECTION

PATENT NO. : 5,462,927

DATED : October 31, 1995

INVENTOR(S) : Jacques-Pierre Moreau and David H. Coy

It is certified that error appears in the above-identified patent and that said Letters Patent is hereby corrected as shown below:

Col. 1, line 3, replace "under a grant of award" to --under a grant or award--;

Col. 1, line 51, replace "The invention also features..." to --The invention features...--;

Col. 3, line 61, replace "BIM-220150." with --BIM-22015.--;

Col. 3, line 62, replace "25°C." with --22°C.--;

Col. 4, line 2, replace "extention digitarum" with --extension digitorium--;

Col. 4, line 28, replace "0.005 mmO" with --0.005 mm.--;

Col. 4, line 44, replace "50 $\mu$g." with --5.0 $\mu$g.--;

Col. 7, line 63, replace "Reicherr" with --Reicherrt--;

Col. 13, line 26 in the heading, replace "- $\mu$g/24 HRS" to -- - 5 $\mu$g/24 HRS--.

Signed and Sealed this

Ninth Day of April, 1996

*Attest:*

BRUCE LEHMAN

*Attesting Officer*  Commissioner of Patents and Trademarks

UNITED STATES PATENT AND TRADEMARK OFFICE
CERTIFICATE OF CORRECTION

PATENT NO. : 5,462,927

DATED : Oct. 31, 1995

INVENTOR(S) : Jacques-Pierre Moreau and David H. Coy

It is certified that error appears in the above-identified patent and that said Letters Patent is hereby corrected as shown below:

Col. 1, delete lines 3-5.

Signed and Sealed this

Twelfth Day of November, 1996

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,462,927

DATED : October 31, 1995

INVENTOR(S) : Jacques-Pierre Moreau and David H. Coy

It is certified that error appears in the above-indentified patent and that said Letters Patent is hereby corrected as shown below:

Col. 1, delete lines 3-5.

Signed and Sealed this

Twenty-second Day of April, 1997

Attest:

BRUCE LEHMAN

*Commissioner of Patents and Trademarks*

*Attesting Officer*